United States Patent
Queiroz et al.

(10) Patent No.: US 9,125,841 B2
(45) Date of Patent: *Sep. 8, 2015

(54) ORAL CARE COMPOSITIONS

(71) Applicant: McNeil-PPC, Inc., Skillman, NJ (US)

(72) Inventors: Daniel Queiroz, Belle Mead, NJ (US); Frank Sun, Branchburg, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 101 days.

This patent is subject to a terminal disclaimer.

(21) Appl. No.: 13/777,379

(22) Filed: Feb. 26, 2013

(65) Prior Publication Data

US 2014/0242003 A1    Aug. 28, 2014

(51) Int. Cl.
| | | |
|---|---|---|
| *A61Q 11/00* | (2006.01) | |
| *A61K 45/06* | (2006.01) | |
| *A61K 8/90* | (2006.01) | |
| *A61K 8/34* | (2006.01) | |
| *A61K 8/37* | (2006.01) | |
| *A61K 8/49* | (2006.01) | |
| *A61K 8/86* | (2006.01) | |

(52) U.S. Cl.
CPC ... *A61K 8/90* (2013.01); *A61K 8/34* (2013.01); *A61K 8/37* (2013.01); *A61K 8/498* (2013.01); *A61K 8/86* (2013.01); *A61Q 11/00* (2013.01)

(58) Field of Classification Search
CPC .......................... A61K 2300/00; A61Q 11/00
USPC ............................................. 424/49; 433/215
See application file for complete search history.

(56) References Cited

U.S. PATENT DOCUMENTS

| | | | |
|---|---|---|---|
| 3,959,458 A | 5/1976 | Agricola | |
| 4,051,234 A | 9/1977 | Gieske | |
| 5,190,747 A | 3/1993 | Sekiguchi | |
| 5,599,527 A | 2/1997 | Hsu | |
| 5,624,906 A * | 4/1997 | Vermeer | 514/23 |
| 6,218,438 B1 | 4/2001 | Alakhov | |
| 6,849,598 B1 | 2/2005 | Lambert, Jr. | |
| 7,084,104 B2 | 8/2006 | Martin | |
| 7,087,650 B2 | 8/2006 | Lennon | |
| 2004/0018154 A1 | 1/2004 | Pan et al. | |
| 2006/0198797 A1* | 9/2006 | Giniger | 424/53 |
| 2007/0190080 A1 | 8/2007 | Friedman | |
| 2011/0089073 A1 | 4/2011 | Baig | |
| 2012/0003162 A1 | 1/2012 | Mordas | |
| 2012/0003163 A1 | 1/2012 | Mordas et al. | |

FOREIGN PATENT DOCUMENTS

| | | |
|---|---|---|
| EP | 2401999 | 1/2012 |
| GB | 2142536 | 1/1985 |
| WO | WO 02/07691 | 1/2002 |

OTHER PUBLICATIONS

Database GNPD [online] Mintel; Jun. 1, 2010, "Mouthwash" XP00272777, Database accession No. 1343978.
Database GNPD [online] Mintel; Dec. 1, 2005, "Mouthwash" XP002727778, Database accession No. 10244301.
PCT International Search Report dated Aug. 21, 2014 for International Application No. PCT/US2014/015723.
Batrakova et al., J. "Optimal Structure Requirements for Pluronic Block Copolymers . . . " Pharmacol Exptl. Therapeu. 2003, vol. 304, No. 2 pp. 845-854.
Kabanov et al., "Micelle Formation and Solubilization of Fluorescent . . . ", Macromolecules 1995, 28, pp. 2303-2314.
Varsheny et al., "Pluronic Microemulsions as Nanoreservoirs . . . ", JACS 2004, 126, pp. 5108-5112.
Chiappetta et al.,"Polyethylene oxide)-poly(propylene oxide) block copolymer . . . " Eur. J. Pharm. Biopharm. 2007, 66, pp. 303-317.

* cited by examiner

*Primary Examiner* — Frederick Krass
*Assistant Examiner* — Tracy Liu

(57) ABSTRACT

The present invention relates to oral compositions, comprising select polyethylene oxide-polypropylene oxide block copolymer surfactants. Methods for using the compositions are also disclosed.

12 Claims, No Drawings

ORAL CARE COMPOSITIONS

FIELD OF THE INVENTION

The present invention relates to oral compositions, comprising select polyethylene oxide-polypropylene oxide block copolymer surfactants. Methods for using the compositions are also disclosed.

BACKGROUND OF THE INVENTION

The formation and stabilization of colloidal dispersion systems have been extensively studied. The stability of these systems can be enhanced by adding a surface active agent or surfactant to modify the interfacial interactions between the components of the system. In selecting the surfactant for such systems, the surfactant's hydrophilic-lipophilic balance (HLB) is traditionally is considered. The HLB scale is based on the relative percentage of hydrophilic to lipophilic groups in the surfactant molecule. For example, an Oil-in-Water (O/W) emulsion would require a high HLB value (e.g., 10-18) to solubilize the molecules in water. The HLB scale by itself, however, fails to indicate whether a specific surfactant will be effective as a delivery agent for active ingredients. In such situations, where the colloidal dispersion system includes active ingredients, the structure of the surfactant molecule should also be considered.

When present, the micelles in a colloidal dispersion system exist in dynamic equilibrium where the rate at which surfactants exchange (or move) between the continuous phase and the micelle phase varies depending on the structure of the surfactant molecule. This rate, in turn, affects the active ingredient's ability to diffuse into/out of the micelles. Without being limited by theory, it is believed that the efficacy of an active ingredient is linked to the active ingredient's ability to diffuse out of the micelles; more specifically, it is believed that the size of hydrophobic chains (for water in oil systems) or hydrophilic chains (for oil in water systems) of surfactants control the ability of active-ingredient, solubilized in a micelle's core, to diffuse in or out of the micelle.

US Patent Publication 2012/0003163 A1 teaches that poloxamers negatively affect the bioavailability of essential oils used as actives ingredients. A nonlimiting theory for this negative effect relates to the number of block units in such poloxamers and the ratio of the polyethylene oxide (PEO) and polypropylene oxide (PPO) blocks, namely poloxamers having higher numbers of PPO blocks and a copolymer length of greater than 30 units (blocks) produces a strong (or increases strength of the) association between the PPO blocks and the active ingredient, locking active ingredient in the core of the micelle and reducing bioavailability.

Because of such negative effects on active ingredient bioavailability, anionic surfactants such as sodium lauryl sulfate (SLS) are typically substituted for poloxamers. Such anionic surfactants have little effect on active ingredient bioavailability as they function as dispersants and not emulsifiers for the essential oils, which allow them to have less of an effect on the bioavailability. In certain situations, however, the use of SLS may be limited in view of its skin/mucosal irritating properties. Poloxamers, on the other hand, are not irritating to skin or mucosal surfaces. There is, therefore, still a need for poloxamers which increase or otherwise improve the bioavailability of active ingredients like the essential oils.

The present inventors have found that PEO-PPO block copolymers having a ratio of PEO and PPO blocks greater than 4 to 1 and a copolymer length less than 30 units reduce the association between the PPO blocks and active ingredients, improving bioavailability.

SUMMARY OF THE INVENTION

It has been discovered that the aforementioned objective can be achieved by the compositions provided herein. In one embodiment, the present invention provides an oral composition comprising:

i. a polyethylene oxide-polypropylene oxide block polymer surfactant of the formula:

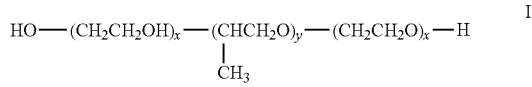

where "x" represents the average number of PEO units and is an integer of from 10 to 100; "y" represents the average number of PPO units and is an integer of less than or equal to 30; and the ratio of "x" to "y" is no greater than 4:1 (or about 4:1);

ii. one or more water-insoluble bioactive agents; and iii. at least one orally acceptable solvent.

In further embodiments, the present invention relates to methods of treating plaque, gingivitis, gum disease, or oral malodor, comprising the step of applying to the tissues (i.e., soft and hard) of the oral cavity of a mammal in need of such treatment the oral composition of the present invention in an amount effective to reduce or prevent tooth decay and/or reduce or prevent the symptoms associated with plaque, gingivitis or gum disease.

In still further embodiments, the present invention relates to methods of treating or reducing symptoms associated with inflamed tissue, comprising the step of applying to the tissues of a mammal in need of such treatment an amount of the composition of the present invention effective to reduce symptoms associated inflammation.

In yet further embodiments, the present invention relates to methods for reducing the number of oral microorganisms responsible for plaque, gingivitis, gum disease or oral malodor, comprising the step of applying to the tissues of the oral cavity of a mammal having such microorganisms an amount of the composition of the present invention effective to reduce the number of such oral microorganisms.

DETAILED DESCRIPTION OF THE INVENTION

The compositions of the present invention can comprise, consist of, or consist essentially of the essential elements and limitations of the invention described herein, as well any of the additional or optional ingredients, components, or limitations described herein. The term "comprising" (and its grammatical variations) as used herein is used in the inclusive sense of "having" or "including" and not in the exclusive sense of "consisting only of."

The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference in their entirety are only incorporated herein to the extent that they are not inconsistent with this specification.

The phrase "orally acceptable" means that the carrier is suitable for application to the surfaces of the oral cavity or ingestion by a living organism including, but not limited to, mammals and humans without undue toxicity, incompatibility, instability, allergic response, and the like.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouth rinse, solutions, mousse, foam, denture care product, mouth spray, lozenge or chewable tablet. The oral care composition may also be incorporated onto floss, strips or films for direct application or attachment to oral surfaces or integrated into a device or applicator such as a toothbrush or roll-ons. Such applicators may be for single or multiple use.

The phrase "reduced level" or "essentially free" of alcohol means an amount of a $C_2$-$C_4$ monohydric alcohol up to 10% v/v (or about 10% v/v), optionally, up to 5% v/v (or about 5% v/v), optionally, up to 1.0% v/v (or about 1.0% v/v), optionally up to 0.1% v/v (or about 0.1% v/v) by volume of the total composition. Optionally, the compositions of the present invention are free of $C_2$-$C_4$ monohydric alcohols.

All percentages, parts and ratios are based upon the total weight of the composition of the present invention, unless otherwise specified. All such weights as they pertain to the listed ingredients are based on the level of the particular ingredient described and, therefore, do not include carriers or by-products that may be included in commercially available materials, unless otherwise specified.

The compositions of the present invention may be in the form of mouth washes, mouth rinses, dentifrices, toothpastes, gels, solutions or strips such as non-peroxide tooth whitening strips and the like.

Polyethylene Oxide-Polypropylene Oxide Block Copolymer Surfactant

Poloxamers are nonionic triblock copolymers composed of a central hydrophobic chain of polypropylene oxide flanked by two hydrophilic chains of polyethylene oxide. Poloxamers are also known by the trade name PLURONIC (BASF, Florham Park, N.J.).

The compositions of the present invention comprise a polyethylene oxide-polypropylene oxide block polymer surfactant of the formula:

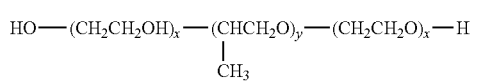

I where "x" represents the average number of PEO units and is an integer of from 10 to 100, optionally 10 to 80, or optionally from 16 to 80; "y" represents the average number of PPO units and is an integer of less than or equal to 30, or optionally from 16 to 30 and the ratio of "x" to "y" is no greater than 4:1 (or about 4:1), optionally 3:1 (or about 3:1), optionally 2.8:1 (or about 2.8:1), optionally 2:1 (or about 2:1), or optionally 1:1 (or about 1:1), yet the ratio of "x" to "y" is at least 0.5:1 (or about 0.5:1), or optionally 0.8:1 (or about 0.8:1). In certain embodiments, the ratio of "x" to "y" is 2.7:1 (or about 2.7:1). In certain embodiments, the ratio of "x" to "y" is 1:1 (or about 1:1).

These products are complex mixtures of copolymers produced in a wide range of molecular weights (1,100-14,000) with varying degrees of ethylene oxide and propylene oxide. The block polymers are prepared by polymerizing propylene oxide in a controlled fashion to give a desired weight followed by ethoxylation with ethylene oxide. Examples of useful poloxamers include, but are not limited to:

| Poloxamer | PLURONIC | "y" (Average No. of PPO units) | "x" (Average No. of PEO units) |
|---|---|---|---|
| 108 | F38 | 17.1 | 18.8 |
| 188 | F68 | 29 | 76.4 |
| 238 | F88 | 39.3 | 103.6 |
| 338 | F108 | 50.3 | 132.7 |
| 407 | F127 | 65.2 | 100.2 |
| 237 | F 87 | 39.8 | 61.3 |
| 335 | P105 | 56 | 36.9 |
| 185 | P 65 | 29.3 | 19.3 |

Further discussion of poloxamers can be found in: Batrakova et al., J. Pharmacol Exptl. Therapeu. 2003, 304, pp. 845-854; U.S. Pat. No. 6,218,438 to Alakhov et al.; U.S. Pat. No. 6,849,598 to Lambert, Jr.; Kabanov et al., Macromolecules 1995, 28, pp. 2303-2314; Varsheny et al., JACS 2004, 126, pp. 5108-5112; and Chiappetta and Sosnik, Eur. J. Pharm. Biopharm. 2007, 66, pp. 3003-3017, each of U.S. Pat. Nos. 6,218,438 and 6,849,598 are herein incorporated by reference in its entirety.

In certain embodiments, the poloxamer is selected from the group consisting of poloxamer 108, poloxamer 188 or mixtures thereof. In still other embodiments, the poloxamer is poloxamer 188.

The PEO-PPO block copolymer surfactant can be present at concentrations of from 0.001% to 15%, optionally 0.01% to 10%, optionally from 0.05% to 5%, or optionally from 0.1% to 3%.

Water-Insoluble Bioactive Agents

The compositions of the present invention also comprise a water-insoluble bioactive agent. Typical examples of such agents, useful when considering anticaries, antiplaque, antigingivitis or gum disease treatment (or symptom reduction) effectiveness, safety and formulation, are:

I. Antimicrobial water-insoluble bioactive agents such as:
Halogenated Diphenyl Ethers
2',4,4'-trichloro-2-hydroxy-diphenyl ether (Triclosan)
2,2'-dihydroxy-5,5'-dibromo-diphenyl ether.
Halogenated Salicylanilides
4'5-dibromosalicylanilide
3,4',5-trichlorosalcylanilide
3,4',5-tribromosalicylanilide
2,3,3',5-tetrachlorosalicylanilide
3,3',5-tetrachlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoro methyl salicylanilide (Flurophene).
Benzoic Esters
Methyl-p-Hydroxybenzoic Ester
Ethyl-p-Hydroxybenzoic Ester
Propyl-p-Hydroxybenzoic Ester
Butyl-p-Hydroxybenzoic Ester.
Halogenated Carbanilides
3,4,4'-trichlorocarbanilide
3-trifluoromethyl-4,4'-dichlorocarbanilide
3,3',4-trichlorocarbanilide.

Phenolic Compounds (including phenol and its homologs, mono- and poly-alkyl and aromatic halo (e.g. F,Cl,Br,I)-phenols, resorcinol and catechol and their derivatives and bisphenolic compounds). Such phenolic compounds includes inter alia:
Phenol and its Homologs
Phenol
2 Methyl-Phenol
3 Methyl-Phenol
4 Methyl-Phenol
4 Ethyl-Phenol
2,4-Dimethyl-Phenol
2,5-Dimethyl-Phenol
3,4-Dimethyl-Phenol
2,6-Dimethyl-Phenol
4-n-Propyl-Phenol
4-n-Butyl-Phenol
4-n-Amyl-Phenol
4-tert-Amyl-Phenol
4-n-Hexyl-Phenol
4-n-Heptyl-Phenol
2-Methoxy-4-(2-Propenyl)-Phenol (Eugenol).
Mono- and Poly-Alkyl and Aralkyl Halophenols
Methyl-p-Chlorophenol
Ethyl-p-Chlorophenol
n-Propyl-p-Chlorophenol
n-Butyl-p-Chlorophenol
n-Amyl-p-Chlorophenol
sec-Amyl-p-Chlorophenol
n-Hexyl-p-Chlorophenol
Cyclohexyl-p-Chlorophenol
n-Heptyl-p-Chlorophenol
n-Octyl-p-Chlorophenol
O-Chlorophenol
Methyl-o-Chlorophenol
Ethyl-o-Chlorophenol
n-Propyl-o-Chlorophenol
n-Butyl-o-Chlorophenol
n-Amyl-o-Chlorophenol
tert-Amyl-o-Chlorophenol
n-Hexyl-o-Chlorophenol
n-Heptyl-o-Chlorophenol
p-Chlorophenol
o-Benzyl-p-Chlorophenol
o-Benzyl-m-methyl-p-Chlorophenol
o-Benzyl-m,m-dimethyl-p-Chlorophenol
o-Phenylethyl-p-Chlorophenol
o-Phenylethyl-m-methyl-p-Chlorophenol
3-Methyl-p-Chlorophenol
3,5-Dimethyl-p-Chlorophenol
6-Ethyl-3-methyl-p-Chlorophenol
6-n-Propyl-3-methyl-p-Chlorophenol
6-iso-Propyl-3-methyl-p-Chlorophenol
2-Ethyl-3,5-dimethyl-p-Chlorophenol
6-sec Butyl-3-methyl-p-Chlorophenol
2-iso-Propyl-3,5-dimethyl-p-Chlorophenol
6-Diethylmethyl-3-methyl-p-Chlorophenol
6-iso-Propyl-2-ethyl-3-methyl-p-Chlorophenol
2-sec Amyl-3,5-dimethyl-p-Chlorophenol
2-Diethylmethyl-3,5-dimethyl-p-Chlorophenol
6-sec Octyl-3-methyl-p-Chlorophenol
p-Bromophenol
Methyl-p-Bromophenol
Ethyl-p-Bromophenol
n-Propyl-p-Bromophenol
n-Butyl-p-Bromophenol
n-Amyl-p-Bromophenol
sec-Amyl-p-Bromophenol
n-Hexyl-p-Bromophenol
cyclohexyl-p-Bromophenol
o-Bromophenol
tert-Amyl-o-Bromophenol
n-Hexyl-o-Bromophenol
n-Propyl-m,m-Dimethyl-o-Bromophenol
2-Phenyl Phenol
4-chloro-2-methyl phenol
4-chloro-3-methyl phenol
4-chloro-3,5-dimethyl phenol
2,4-dichloro-3,5-dimethylphenol
3,4,5,6-terabromo-2-methylphenol
5-methyl-2-pentylphenol
4-isopropyl-3-methylphenol
5-chloro-2-hydroxydiphenylemthane.
Resorcinol and its Derivatives
Resorcinol
Methyl-Resorcinol
Ethyl-Resorcinol
n-Propyl-Resorcinol
n-Butyl-Resorcinol
n-Amyl-Resorcinol
n-Hexyl-Resorcinol
n-Heptyl-Resorcinol
n-Octyl-Resorcinol
n-Nonyl-Resorcinol
Phenyl-Resorcinol
Benzyl-Resorcinol
Phenylethyl-Resorcinol
Phenylpropyl-Resorcinol
p-Chlorobenzyl-Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4'-Bromo-2,4-Dihydroxydiphenyl Methane.
Bisphenolic Compounds
Bisphenol A
2,2'-methylene bis(4-chlorophenol)
2,2'-methylene bis(3,4,6-trichlorophenol)(hexachlorophene)
2,2'-methylene bis(4-chloro-6-bromophenol)
bis(2-hydroxy-3,5-dichlorophenyl)sulfide
bis(2-hydroxy-5-chlorobenzyl)sulfide.

Other antimicrobial water-insoluble bioactive agents include, but are not limited to: hexetidine; fatty acid compounds such as caproic acid, caprilic acid, capric acid, lauric acid, myristic acid, myristoleic acid, palmitic acid, palmitoleic acid, stearic acid, oleic acid, elaidic acid, linoleic acid, linolenic acid, linolelaidic acid, arachidonic acid vitamin E, vitamin E acetate, apigenin and mixtures thereof and long chain fatty alcohols such as described in US Patent publication US 20110123462 to Mordas et al., herein incorporated by reference in its entirety, (examples of which include, but are not limited to 1-decen-3-ol; cis-4-decen-1-ol, trans-2-decen-1-ol, cis-2-nonen-1-ol, cis-4-decenal, trans-2-decenal, cis-7-decenal, cis-5-octen-1-ol, trans-2-octen-1-ol, 1-octen-3-ol, cis-3-nonen-1-ol, trans-2-nonen-1-ol, cis-6-nonen-1-ol, 9-decen-1-ol, trans-2-undecen-1-ol, trans-2-dodecen-1-ol, trans-2-octenal, trans-2-nonenal, 6-nonenal, cis-2-decenal, trans-2-undecenal, trans-2-dodecenal, cis-3-octen-1-ol, 3-octen-2-ol, 10-undecen-1-ol, trans-2-tridecen-1-ol, stereoisomers thereof and mixtures thereof). Oils such as peppermint oil and sage oil are also useful herein.

Also useful as antimicrobial water-insoluble bioactive agents are one or more bioactive essential oils or mixtures thereof. Nonlimiting examples of such essential oils include:

Thymol, [(CH$_3$)$_2$CHC$_6$H$_3$(CH$_3$)OH, also known as isopropyl-m-cresol], is only slightly soluble in water but is soluble in alcohol; Methyl salicylate, [C$_6$H$_4$OHCOOCH$_3$, also known as wintergreen oil], additionally provides flavoring to the together with its antimicrobial function;

Eucalyptol (C$_{10}$H$_{18}$O, also known as cineol) is a terpene ether and provides a cooling, spicy taste. Eucalyptol may be used in place of thymol in certain formulations in the same amount if desired; and Menthol (CH$_3$C$_6$H$_9$(C$_3$H$_7$)OH), also known as hexahydrothymol) is also only slightly soluble in alcohol, and is fairly volatile. Menthol, in addition to any antiseptic properties, provides a cooling, tingling sensation.

II. Anti-inflammatory Water-insoluble Bioactive Agents Such as:

NFkB-inhibitor such as substituted resorcinols (such as 4-hexyl resorcinol and 4-octylresorcinol), (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts of Paulownia tomentosa wood, and combinations thereof; phellodendron *amurense* cortex extract (PCE), feverfew (*Tanacetum parthenium*), ginger (*Zingiber officinale*), ginko (*Ginko Biloba*), cotinus (*Cotinus coggygria*), goji berry (*Lycium barbarum*), milk thistle extract (*Silybum marianum*), honeysuckle (*Lonicera japonica*), basalm of Peru (*Myroxylon pereirae*), sage (*Salvia officinalis*), cranberry extract (*Vaccinium oxycoccos*), amaranth oil (*Amaranthus cruentus*), pomegranate (*Punica granatum*), yerbe mate (*Ilex paraguariensis* Leaf Extract), white lily flower extract (*Lilium Candidum*), olive leaf extract (*Olea europaea*), phloretin (apple extract), lifenol (hops: *Humulus lupulus*) extract, licochalcone (licorice: *Glycyrrhiza* inflate extract ingredient), symrelief (bisabolol and ginger extract), Magnolol (extract from bark of the *Houpu magnolia [Magnolia officinalis*], Honokiol (extract from cones, bark, and leaves of *Magnolia grandifloris*] and mixtures thereof; non-steroidal anti-inflammatory agents such as salicylic acid derivatives (e.g. aspirin) paraminophenol derivative (e.g. acetaminophen) indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone) and mixtures thereof.

Other useful water-insoluble bioactive agents can be found in US Patent Publication 2007/0190080 to Doron Friedman and US Patent Publication 20120003162 to Mordas et al., each of which is herein incorporated by reference in its entirety.

Optionally, mixtures of any of the above mentioned compounds can be used as the water-insoluble bioactive agent.

The water-insoluble bioactive agent is present in the oral composition in an amount effective to achieve biologic activity such as anti-inflammation, analgesic, anticaries, antiplaque, antigingivitis or reduction in the symptoms of gum disease. The effective amount of the water-insoluble bioactive agent for i) treating or reducing inflammation or other symptoms of gum disease or ii) providing analgesia, anticaries, antiplaque, antigingivitis ranges from about 0.01%, optionally from about 0.01% to about 5%, optionally from about 0.03% to about 1%, or optionally from about 0.03% to about 0.5%, by weight of the total composition. In certain embodiments, the bioactive agent is water-insoluble, or substantially water-insoluble, meaning that its solubility is less than about 1% by weight in water at 25° C. or, optionally, less than about 0.1%.

In certain embodiments, the bioactive essential oils are used in amounts effective to provide antimicrobial activity in the oral cavity. In certain embodiments, the bioactive essential oils are used in amounts effective to provide analgesic or anti-inflammatory activity in the oral cavity. In specific embodiments, the total amount of bioactive essential oils present in the disclosed compositions can be from 0.001% (or about 0.001%) to 0.35% (or about 0.35%) w/v, or optionally from 0.16% (or about 0.16%) to 0.28% (or about 0.28%) w/v of the composition.

In some embodiments, the compositions of the present invention contains a bioactive essential oil selected from the group consisting of thymol, eucalyptol, menthol, methyl salicylate, or/and mixtures thereof. In certain embodiments, the composition contains all four of these bioactive essential oils.

In certain embodiments, thymol is employed in amounts of from 0.001% (or about 0.001%) to 0.25% (or about 0.25%) w/v, or optionally from 0.04% (or about 0.04%) to 0.07% (or about 0.07%) w/v of the composition. In certain embodiments, eucalyptol may be employed in amounts of from 0.001% (or about 0.001%) to 0.11% (or about 0.11%) w/v, or optionally from 0.085% (or about 0.085%) to 0.10% (or about 0.10%) w/v of the composition. In certain embodiments, menthol is employed in amounts of from 0.001% (or about 0.001%) to 0.25% (or about 0.25%) w/v, or optionally from 0.035% (or about 0.035%) to 0.05% (or about 0.05%) w/v of the composition. In certain embodiments, methyl salicylate is employed in amounts of from 0.001% (or about 0.001%) to 0.08% (or about 0.08%) w/v, or optionally from 0.04% (or about 0.04%) to 0.07% (or about 0.07%) w/v of the composition.

Orally Acceptable Solvent

The compositions of the present invention further comprise an orally acceptable solvent. Orally acceptable solvents include, but are not limited to, water, C$_2$-C$_4$ monohydric alcohols, propylene glycol, and mixtures thereof. When present, the C$_2$-C$_4$ monohydric alcohols are at a reduced level.

Optional Components

In certain embodiments, the compositions of the present invention exhibit a high level of antimicrobial activity as measured by an M-factor greater than 0.5 (or about 0.5), optionally 1.0 (or about 1.0) optionally, 2.0 (or about 2.0), or optionally 3.0 (or about 3.0) where "M-factor" equals the log RLU (relative light units) value of water used as the negative control minus the log RLU value of the mouth rinse composition being tested. In still other embodiments, the oral mouth rinse compositions of this invention are clear (to the unaided human eye) and aesthetically appealing products.

The compositions of the present invention may further comprise optional components (collectively referred to as orally acceptable carriers or excipients) which are described in the following paragraphs along with non-limiting examples. These orally acceptable carrier materials include one or more compatible solid or liquid excipients or diluents which are suitable for topical oral administration. By "compatible" is meant that the components of the composition are capable of being commingled without interaction in a manner which would substantially reduce composition stability and/or efficacy. Suitable carriers or excipients are well known in the art. Their selection will depend on secondary considerations like taste, cost, and shelf stability, etc. Although a general list of optional components is provided below, a more detailed discussion of suitable optional components (including excipients and carriers) can be found in US Patent Publication 20110089073 to Baig et al.; U.S. Pat. No. 5,599,527 to Hsu et al.; and US Patent Publication 20120003163 to Mordas et al., each of which is herein incorporated by reference in its entirety.

Additional Surfactant

In certain embodiments, the present invention contains a surfactant in addition to the PEO-PPO block polymer surfactant of the formula I to aid in solubilization of essential oils if present, provided such additional surfactants do not affect the bioavailability of the essential oils. Suitable examples include anionic surfactants, nonionic surfactants, amphoteric surfactants and mixtures thereof.

Anionic surfactants useful herein include, but are not limited to, sarcosine type surfactants or sarcosinates; taurates such as sodium methyl cocoyl taurate; alkyl sulfates such as sodium trideceth sulfate or sodium lauryl sulfate; sodium lauryl sulfoacetate; sodium lauroyl isethionate; sodium laureth carboxylate; sodium dodecyl benzenesulfonate and mixtures thereof. Many suitable anionic surfactants are disclosed in U.S. Pat. No. 3,959,458, to Agricola, et al., herein incorporated by reference in its entirety.

Nonionic surfactants which can be used in the compositions of the present invention include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; ethoxylated hydrogenated castor oils available commercially for example under the trade name CRODURET (Croda Inc., Edison, N.J.), and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium lauroamphoacetate and mixtures thereof. Mixtures of any of the above mentioned surfactants can also be employed. A more detailed discussion of anionic, nonionic and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

The compositions of the present invention may also include one or more optional ingredients nonexclusively including a thickening agent, humectants, chelating agents, whitening agents, and additives such as colorants or dyes, flavorants, preservatives, pH adjusting agents, and the like.

The pH of the compositions of this invention is optionally maintained at range of below 5 (or about 5), optionally, below 4.5 (or about 4.5) or, optionally, in the range of from 4.4 (or about 4.4) to 3 (or about 3), or optionally in the range of from 3.5 (or about 3.5) to 4.2 (or about 4.2).

Commercially available thickening agents capable of imparting the appropriate viscosity to the compositions are suitable for use in this invention. Examples of suitable thickening agents nonexclusively include: mono or diesters of 1) polyethylene glycol of formula: $HO—(CH_2CH_2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the trade name, "PEG 6000 DS".

Commercially available humectants are suitable for use in the present invention. The humectant may be present in an amount of from about 0 percent to about 20%, optionally from about 0.5% to about 15%, or optionally from about 0.5% to about 10%, based on the overall weight of the composition. Examples of suitable humectants nonexclusively include: 1) water soluble liquid polyols selected from the group comprising or consisting or sorbital, glycerine, propylene glycol, hexylene glycol, butylene glycol, dipropylene glycol, and mixtures thereof; 2) polyalkylene glycol of the formula: $HO—(R''O)_b—H$, wherein R'' is an alkylene group having from about 2 to about 3 carbon atoms and b is an integer of from about 2 to about 10; 3) polyethylene glycol ether of methyl glucose of formula $CH_3—C_6H_{10}O_5—(OCH_2CH_2)_c—OH$, wherein c is an integer from about 5 to about 25; 4) urea; and 5) mixtures thereof, In certain embodiments, the humectant is a mixture sorbitol and propylene glycol.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the trade name, "Versene 100XL" and is present in an amount, based upon the total weight of the composition, from about 0 to about 0.5 percent, and preferably from about 0.05 percent to about 0.25 percent.

Suitable preservatives include, sodium benzoate, and polysorbate and are present in the composition in an amount, based upon the total weight of the composition, from about 0 to about 0.2 percent, and preferably from about 0.05 percent to about 0.10 percent.

In certain embodiments, the compositions of the present invention are free of or essentially free of bioavailability affecting compounds. As used herein, "bioavailability affecting compound", means compounds that negatively affect the bioavailability of any incorporated essential oils such as by binding the essential oils or otherwise inactivating the essential oils. "Essentially free" as used with respect to bioavailability affecting compounds is defined as formulations having less than 5% (or about 5%), optionally, 3% (or about 3%), optionally, 1% (or about 1%), or optionally 0.1, or optionally, 0.01% (or about 0.01%), by weight (w/v) of the total composition of a bioavailability affecting compound. In certain embodiments, the bioavailability affecting compound can include, but is not limited to, polyethylene oxide/polypropylene oxide block copolymers falling outside the scope of formula I (as described above); cyclodextrins; polysorbates such as Tweens; and mixtures thereof.

The above described compositions may be prepared by combining the desired components in a suitable container and mixing them under ambient conditions using conventional mixing technology, including technology well known in the art, such as by a mechanically stirred propeller, paddle, and the like. The order of mixing is not critical.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof

EXAMPLES

The following examples are formed using conventional mixing technology and are illustrative only and should not be construed as limiting the invention in any way. Those skilled in the art will appreciate that variations are possible which are within the spirit and scope of the appended claims.

In order to evaluate different poloxamer samples, the concentration of the poloxamer samples are normalized based on the contribution (i.e., number) of hydrophobic PPO units. Without being limited by theory, it is believed that the hydrophobic PPO unit segments interact with the bioactive agent (e.g., essential oils) of the present invention to keep them emulsified and dispersed and the strength of this interaction (or the number of interacting PPO units) determines whether or not the bioactive agent is inactivated (i.e., bound) or allowed to remain efficacious (i.e., unbound or substantially unbound). Thus, the concentration of all poloxamer samples per formulation is adjusted to provide a hydrophobicity equal to that of about 1.5 wt % poloxamer F68, this permits for a comparison of the relative amounts of various poloxamers required to achieve efficacy (i.e., essential oil interaction) similar to that of poloxamer F68. This 1.5 wt % concentration of poloxamer F68 was chosen as the standard formula concentration made since formulations containing such a concentration of poloxamer F68 exhibit good efficacy (see results Example I).

Example I

| Ingredients | A (% w/w) | B (% w/w) | C (% w/w) | D (% w/w) | E (% w/w) | F (% w/w) | G (% w/w) | H (% w/w) |
|---|---|---|---|---|---|---|---|---|
| Propylene Glycol USP | 7.000000 | 7.000000 | 7.000000 | 7.000000 | 7.000000 | 7.000000 | 7.000000 | 7.000000 |
| Benzoic Acid USP | 0.085900 | 0.085900 | 0.085900 | 0.085900 | 0.085900 | 0.085900 | 0.085900 | 0.085900 |
| Menthol, USP | 0.041262 | 0.041262 | 0.041262 | 0.041262 | 0.041262 | 0.041262 | 0.041262 | 0.041262 |
| Thymol, NF | 0.062039 | 0.062039 | 0.062039 | 0.062039 | 0.062039 | 0.062039 | 0.062039 | 0.062039 |
| Methyl Salicylate, NF | 0.064078 | 0.064078 | 0.064078 | 0.064078 | 0.064078 | 0.064078 | 0.064078 | 0.064078 |
| Eucalyptol, USP | 0.089515 | 0.089515 | 0.089515 | 0.089515 | 0.089515 | 0.089515 | 0.089515 | 0.089515 |
| Purified Water | 77.509307 | 77.509307 | 77.509307 | 77.509307 | 77.509307 | 77.509307 | 77.509307 | 77.509307 |
| Sodium Saccharin USP, granular | 0.060600 | 0.060600 | 0.060600 | 0.060600 | 0.060600 | 0.060600 | 0.060600 | 0.060600 |
| Sucralose powder, NF | 0.010000 | 0.010000 | 0.010000 | 0.010000 | 0.010000 | 0.010000 | 0.010000 | 0.010000 |
| Sodium Benzoate, NF | 0.077300 | 0.077300 | 0.077300 | 0.077300 | 0.077300 | 0.077300 | 0.077300 | 0.077300 |
| Sorbitol solution 70% USP | 10.000000 | 10.000000 | 10.000000 | 10.000000 | 10.000000 | 10.000000 | 10.000000 | 10.000000 |
| PLURONIC F 108 | — | 0.863010 | — | — | — | — | — | — |
| PLURONIC F 88 | — | — | 1.10526 | — | — | — | — | — |
| PLURONIC F 87 | — | — | — | 1.09091 | — | — | — | — |
| PLURONIC F 68 | — | — | — | — | 1.50000 | — | — | — |
| PLURONIC F 127 | 0.66667 | — | — | — | — | — | — | — |
| PLURONIC F 38 | — | — | — | — | — | 2.80000 | — | — |
| PLURONIC P 105 | — | — | — | — | — | — | 0.77538 | — |
| PLURONIC P 65 | — | — | — | — | — | — | — | 1.44000 |
| Purified Water | QS to 100% | QS to 100% | QS to 100% | QS to 100% | QS to 100% | QS to 100% | QS to 100% | QS to 100% |

The procedure for mixing the formulations of Example 1 is as follows:

Into a suitable container, an aqueous phase is prepared by adding the water, saccharin, sucralose and sodium benzoate and mixed until the ingredients are dissolved and the solution uniform and homogeneous. Next, the sorbitol solution is added and mixed until the solution uniform and homogeneous.

Into a separate suitable container, a glycol solution is prepared by adding separately, with mixing until dissolved, each of, the propylene glycol, benzoic acid, menthol and thymol. Next, the methyl salicylate and eucalyptol are added and mixed for 5 minutes or until the solution uniform and homogeneous.

To the aqueous is added the poloxamer with mixing until the solution uniform and homogeneous. Next the glycol solution is added with mixing until the solution uniform and homogeneous. Additional water is added as necessary to QS to appropriate levels. The pH is adjusted to 4.2±0.1 with minimum amounts of HCl or NaOH as necessary. The turbidity of each of formulations A-H is measured using a Laboratory Turbidimeter Model 2100N from Hach Company (Loveland, CO).

The formulations A-H are also tested using an in-vitro single species S. mutans biofilm model. A 22-hour S. mutans biofilm is grown (N=96) and exposed to the formulations as well as positive and negative controls for 30 seconds. Sterile water was used as the negative control. After treatment the biofilm is neutralized and rinsed. The biofilm is harvested via sonication using a Misonix XL-2000 Ultrasonic processor (Qsonica, LLC, Newtown, Conn.). Using a Celsis Rapid Detection RapiScreen kit (Celsis International PLC, Chicago), the bacteria was lysed with Celsis Luminex and the ATP from the bacteria was measured using the bioluminescence marker Celsis LuminATE. Decreasing log RLUs (relative light units) indicates fewer bacteria alive after treatment. Sterile water is used as the negative control and, using the above method, the Log RLU was determined to be 7.74.

| | A (% w/w) | B (% w/w) | C (% w/w) | D (% w/w) | E (% w/w) | F (% w/w) | G (% w/w) | H (% w/w) |
|---|---|---|---|---|---|---|---|---|
| pH | 4.11 | 4.15 | 4.13 | 4.2 | 4.17 | 4.12 | 4.18 | 4.19 |
| Turbidity (NTU) | 10.8 | 9.88 | 5.71 | 5.5 | 6.19 | 3994 | 12.2 | 469 |
| log RLU | 7.45 | 7.29 | 7.37 | 7.52 | 6.81 | 6.76 | 7.77 | 7.88 |
| M-factor | 0.29 | 0.45 | 0.37 | 0.22 | 0.93 | 0.98 | −0.03 | −0.14 |

Example II

| Ingredient | Comparative Example Essential Oil Toothpaste (% w/w) | Inventive Toothpaste Example I (% w/w) | Inventive Toothpaste Example J (% w/w) |
|---|---|---|---|
| Methyl Salicylate NF | 0.51600 | 0.51600 | 0.51600 |
| Eucalyptol | 0.77450 | 0.77450 | 0.77450 |
| Flavor | 0.22500 | 0.22500 | 0.22500 |
| Thymol NF | 0.51120 | 0.51120 | 0.51120 |
| Menthol USP | 0.34000 | 0.34000 | 0.34000 |
| Purified Water | 24.49855 | 21.22347 | 14.97347 |
| Sorbitol Solution | 40.00000 | 40.00000 | 40.00000 |
| Color | 0.00225 | 0.00000 | 0.00000 |
| Disodium Phosphate | 0.03000 | 0.03000 | 0.03000 |
| Sodium Monofluorophosphate USP | 0.76000 | 0.76000 | 0.76000 |
| Sodium Saccharin USP Granular | 1.20000 | 1.20000 | 1.20000 |
| Sodium Phosphate Monobasic Anhydrous | 0.25000 | 0.25000 | 0.25000 |
| Polyethylene Glycol 32 NF | 3.00000 | 3.00000 | 3.00000 |
| Benzoic Acid | 0.15000 | 0.15000 | 0.15000 |
| Phosphoric Acid NF | 0.44250 | 0.44250 | 0.44250 |
| Hydrated Silicon Dioxide | 7.00000 | 7.00000 | 7.00000 |
| Silica Amorphous Sylodent 750 | 11.00000 | 11.00000 | 11.00000 |
| Glycerin USP, 96% | 6.00000 | — | — |
| Glycerin USP, 99.7% | — | 5.77733 | 5.77733 |
| Sodium Carboxymethylcellulose (CMC) | 1.20000 | 1.20000 | 1.20000 |
| Xanthan Gum K6B166 | 0.25000 | 0.25000 | 0.25000 |
| Titanium Dioxide | 0.35000 | 0.35000 | 0.35000 |
| PLURONIC F127 | — | 5.00000 | — |
| PLURONIC F68 | — | — | 11.25000 |
| Sodium Lauryl Sulfate W&D | 1.50000 | — | — |
| Total | 100.00000 | 100.00000 | 100.00000 |

The procedure for mixing the toothpaste formulations of Example II is as follows:

Into a suitable container, a flavor blend is prepared by adding the following ingredients with mixing the methyl salicylate, flavor, thymol and menthol. The container is covered to prevent flavor loss. Just prior to transfer, the eucalyptol is added and blend is mixed until the solution uniform and homogeneous.

Into a suitable container, a humectant phase is prepared by adding the following ingredients with mixing the glycerin and sodium CMC. The humectant phase is mixed until uniform and homogeneous. Next, the xanthan gum is added and mixed until the phase mixture is uniform and homogeneous.

Into a suitable container, an aqueous phase is prepared by adding the following ingredients with mixing the purified water, PLURONIC and sorbitol. The aqueous phase is mixed until uniform and homogeneous. Next, the sodium monoflourophosphate USP, sodium saccharin, sodium phosphate (monobasic) anhydrous, sodium phosphate dibasic (anhydrous), polyethylene glycol 32 NF, benzoic acid USP are added and mixed for about 10 minutes until the phase mixture is uniform and homogeneous. The phosphoric acid is added and mixed until the phase mixture is uniform and homogeneous.

Into the container containing the aqueous phase, the humectants phase is added with mixing until uniform and homogeneous. The titanium dioxide is added to the mixture and mixed until the mixture is uniform and white. The mixture is transferred to a Ross mixer (Model No.: DPM-1QT, Charles Ross & Son Company [Hauppauge, New York]) and the Zeosyl 200 is added. The mixture is mixed at 15 RPM for about 2 minutes until powders are wetted out. The mixture is then mixed at 40-50 RPM for about 5 minutes under vacuum. The sylodent 750 is added the mixture and mixed at 15 RPM for about 2 minutes until powders are wetted out. The mixture is then mixed at 40-50 RPM for about 5 minutes under vacuum. The flavor blend is added to the mixture and mixed at 25 RPM for about 2 minutes until flavors are uniformly dispersed. The mixture placed under vacuum and mixing is continued for about 15 to about 20 minutes until the paste is of appropriate consistency. Once consistency is achieved, the mixing is stopped, the vacuum is removed and the toothpaste is dispensed into primary packaging tubes.

An ex vivo kill kinetics assay is performed using conventional testing methodology to evaluate antimicrobial effect of the various poloxamers in the toothpaste formulations of Example II. The assay involved testing the toothpaste formulation of Example II against pooled human saliva ex-vivo at 30 seconds and 1 minute exposure times to understand the differences between PLURONIC F127 and PLURONIC F68. A commercial essential oil toothpaste is included as a positive control in the assay. Sterile water was used as negative control in this test.

Method:
- A sample is weighed into a sterile test tube containing three glass beads;
- Pooled human saliva is added to the test tube and vortexed;
- at 30 and 60 seconds, an aliquot is taken and neutralized to stop the activity of the antimicrobials;
- serial dilutions are prepared and samples are plated on tryptic soy agar (TSA) with 5% sheep's blood with with vitamin K-hemin for total microorganism counts and Oral Organisms Producing Sulfide (OOPS) III agar for counts of malodor microorganisms.
- after incubation, total recoverable colonies are enumerated and compared to colony forming units in a negative control group.
- Samples are tested in triplicate; the results represent the average of the three replicates.

Results of the ex vivo kill kinetics assay are shown in Table 1 (as % reduction from sterile water):

TABLE 1

| | Essential Oil Mouth rinse (% reduction vs. sterile water) | I (% reduction vs. sterile water) | J (% reduction vs. sterile water) |
|---|---|---|---|
| Malodor associated counts on OOPs III agar | | | |
| 0.5 minute | 99.9% | 99.9% | 99.9% |
| 1.0 minute | 99.9% | 99.9% | 99.9% |
| Total counts on TSA with 5% sheep's blood agar with HK | | | |
| 0.5 minute | 99.9% | 97.5% | 99.9% |
| 1.0 minute | 99.9% | 94.2% | 99.9% |

Example III

Further mouthwash experiments were conducted to validate the principle governing the ability of nonionic surfactants to work as an effective in-situ delivery agent for bioactive agents. The results below demonstrate the effectiveness of poloxamers having less than 30 units of the polypropylene oxide blocks. Table 2 shows improved performance for formulations free of and/or essentially free of SLS and containing an antimicrobially effective amount of one or more essential oil bioactive agents.

TABLE 2

| Ingredients | Negative Control (% w/w) | Positive Control (commercially available essential oil mouth rinse) (%w/w) | K (% w/w) | L (% w/w) | M (% w/w) | N (% w/w) |
|---|---|---|---|---|---|---|
| Purified Water USP | 100.0000 | 82.0950 | 80.4450 | 80.9450 | 81.9830 | 80.9950 |
| PLURONIC F127 | — | 0.2000 | 2.0000 | — | 0.5000 | — |
| PLURONIC F68 | — | — | — | 1.5000 | — | 1.5000 |
| Sodium Lauryl Sulfate | — | 0.2000 | 0.0500 | 0.0500 | 0.0120 | — |
| Sodium Benzoate | — | 0.0773 | 0.0773 | 0.0773 | 0.0773 | 0.0773 |
| Sweetener | — | 0.0706 | 0.0706 | 0.0706 | 0.0706 | 0.0706 |
| Propylene Glycol | — | 7.0000 | 7.0000 | 7.0000 | 7.0000 | 7.0000 |
| Benzoic Acid | — | 0.0859 | 0.0859 | 0.0859 | 0.0859 | 0.0859 |
| Menthol | — | 0.0385 | 0.0385 | 0.0385 | 0.0385 | 0.0385 |
| Thymol | — | 0.0620 | 0.0620 | 0.0620 | 0.0620 | 0.0620 |
| Eucalyptol | — | 0.0895 | 0.0895 | 0.0895 | 0.0895 | 0.0895 |
| Methyl Salicylate | — | 0.0641 | 0.0641 | 0.0641 | 0.0641 | 0.0641 |
| Flavor | — | 0.0170 | 0.0170 | 0.0170 | 0.0170 | 0.0170 |

TABLE 2-continued

| Ingredients | Negative Control (% w/w) | Positive Control (commercially available essential oil mouth rinse) (%w/w) | K (% w/w) | L (% w/w) | M (% w/w) | N (% w/w) |
|---|---|---|---|---|---|---|
| Sorbitol (70% solution) | — | 10.0000 | 10.0000 | 10.0000 | 10.0000 | 10.0000 |
| Color | — | 0.000020 | — | — | — | — |
| Total | 100 | 100 | 100 | 100 | 100 | 100 |
| pH | — | — | 4.22 | 4.21 | 4.22 | 4.22 |
| Turbidity (NTU) | — | — | 4.96 | 2.47 | 11.4 | 7.51 |
| log RLU | 7.81 | 5.72 | 7.79 | 6.88 | 7.29 | 6.93 |
| M-factor | 0 | 2.09 | 0.02 | 0.93 | 0.52 | 0.88 |

What is claimed is:

1. A composition, comprising:
  i. a polyethylene oxide-polypropylene oxide block polymer surfactant of the formula:

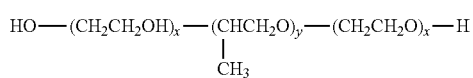

I where "x" represents the average number of polyethylene oxide units and is an integer of from 10 to 100; "y" represents the average number of polypropylene oxide units and is an integer of less than or equal to 30; and the ratio of "x" to "y" is no greater than about 4:1 but at least 0.8:1, and wherein the polymer surfactant of formula I is selected from the group consisting of poloxamer 108, poloxamer 188 or mixtures thereof;
  ii. one or more water-insoluble bioactive agents; and
  iii. at least one orally acceptable solvent; said composition having a pH below 5.

2. The composition according to claim 1 wherein the polymer surfactant is poloxamer 188.

3. The composition according to claim 1 wherein the one or more water-insoluble bioactive agents is a bioactive essential oil.

4. The composition according to claim 3 wherein the bioactive essential oil is selected from the group consisting of thymol, eucalyptol, menthol, methyl salicylate and mixtures thereof.

5. The composition according to claim 4 wherein the bioactive essential oil is a mixture of thymol, eucalyptol, menthol and methyl salicylate.

6. The composition according to claim 1 wherein the composition is essentially free of $C_2$-$C_4$ monohydric alcohols.

7. The composition according to claim 6 wherein the composition is free of $C_2$-$C_4$ monohydric alcohols.

8. The composition according to claim 1 wherein the composition is an oral composition.

9. A method of treating plaque, gingivitis, gum disease or oral malodor, comprising the step of applying to the tissues of the oral cavity of a mammal in need of such treatment an amount of the composition of claim 1 effective to reduce symptoms associated with plaque, gingivitis, gum disease or oral malodor.

10. A method for reducing the number of oral microorganisms responsible for plaque, gingivitis, gum disease or oral malodor, comprising the step of applying to the tissues of the oral cavity of a mammal having such microorganisms an amount of the composition of claim 1 effective to reduce the number of such oral microorganisms.

11. The method of claim 10 wherein application of the composition to the oral cavity results in an M-factor of greater than about 0.5.

12. The composition of claim 1 having a pH of below 4.5.

* * * * *